(12) United States Patent
Shin

(10) Patent No.: US 11,654,078 B2
(45) Date of Patent: May 23, 2023

(54) BEAUTY TREATMENT WATER GENERATOR AND BEAUTY TREATMENT DEVICE USING SAME

(71) Applicant: Sung Bok Shin, Seoul (KR)

(72) Inventor: Sung Bok Shin, Seoul (KR)

( * ) Notice: Subject to any disclaimer, the term of this patent is extended or adjusted under 35 U.S.C. 154(b) by 546 days.

(21) Appl. No.: 16/637,728

(22) PCT Filed: Aug. 9, 2018

(86) PCT No.: PCT/KR2018/009102
§ 371 (c)(1),
(2) Date: Feb. 7, 2020

(87) PCT Pub. No.: WO2019/031878
PCT Pub. Date: Feb. 14, 2019

(65) Prior Publication Data
US 2020/0170879 A1    Jun. 4, 2020

(30) Foreign Application Priority Data

Aug. 10, 2017 (KR) .................. 10-2017-0101847

(51) Int. Cl.
*A61H 15/02* (2006.01)
*A61N 1/30* (2006.01)
(Continued)

(52) U.S. Cl.
CPC .......... *A61H 15/02* (2013.01); *A45D 34/041* (2013.01); *A61H 23/02* (2013.01); *A61N 1/328* (2013.01); *A61N 5/0616* (2013.01)

(58) Field of Classification Search
CPC ............... A61H 15/02; A61H 2201/10; A61H 2201/105; A61H 2015/0042;
(Continued)

(56) References Cited

U.S. PATENT DOCUMENTS 3,163,166 A * 12/1964 Migliarese ............. A61N 1/303
                                                                401/209
5,931,859 A *  8/1999 Burke ..................... A61N 1/322
                                                                 604/20
(Continued)

FOREIGN PATENT DOCUMENTS

GB        2372705 A  *  9/2002  ............... A61N 1/30
KR        10-0794575           1/2008
(Continued)

OTHER PUBLICATIONS

English Specification of 10-0794575.
(Continued)

*Primary Examiner* — Justine R Yu
*Assistant Examiner* — Christopher E Miller
(74) *Attorney, Agent, or Firm* — Antonio Ha & U.S. Patent, LLC

(57) ABSTRACT

Disclosed is a beauty treatment device including: an upper portion; a lower portion; a handle formed on the lower portion; a hollow hole formed in the upper portion; a conductive holder configured in the hollow hole; and a beauty treatment water generator detachably attachable to the conductive holder, wherein at least a part of the beauty treatment water generator is configured as a conductor so that, when the beauty treatment water generator is inserted into the conductive holder and beauty treatment water flowing out of the beauty treatment water generator contacts human skin, micro-currents, which are generated in the beauty treatment device and flow through a beauty treatment water, can flow through human skin after passing through the conductive holder and the conductor.

5 Claims, 11 Drawing Sheets

(51) Int. Cl.
*A45D 34/04* (2006.01)
*A61H 23/02* (2006.01)
*A61N 1/32* (2006.01)
*A61N 5/06* (2006.01)

(58) Field of Classification Search
CPC ............ A61H 2015/0064; A45D 34/04; A45D 34/041; A45D 40/261; A45D 2200/202; A61N 1/322; A61N 1/325; A61N 1/328; A61N 1/0428; A61N 5/0616
See application file for complete search history.

(56) References Cited

U.S. PATENT DOCUMENTS

| | | | | |
|---|---|---|---|---|
| 2005/0191252 | A1* | 9/2005 | Mitsui | A61H 23/0245 601/1 |
| 2005/0234516 | A1* | 10/2005 | Gueret | A61N 1/325 607/3 |
| 2005/0267399 | A1* | 12/2005 | Tedoldi | A61N 1/325 604/20 |
| 2008/0262394 | A1* | 10/2008 | Pryor | A61H 15/02 601/15 |
| 2010/0274329 | A1* | 10/2010 | Bradley | A61N 1/328 607/90 |
| 2012/0165710 | A1* | 6/2012 | Nichols | A61H 23/0263 601/72 |
| 2013/0158547 | A1* | 6/2013 | David | A61B 17/00 606/41 |
| 2013/0253412 | A1* | 9/2013 | Yanaki | A61N 1/0428 604/20 |
| 2015/0360014 | A1* | 12/2015 | Decaux | A45D 34/04 604/20 |
| 2016/0310728 | A1* | 10/2016 | Cazares Delgadillo | A61N 1/0428 |
| 2018/0168318 | A1* | 6/2018 | Streeter | A45D 40/18 |

FOREIGN PATENT DOCUMENTS

| | | |
|---|---|---|
| KR | 10-0962973 | 6/2010 |
| KR | 10-1695411 | 1/2017 |
| KR | 10-1706014 | 2/2017 |
| KR | 10-1713583 | 3/2017 |
| KR | 10-2017-0043080 | 4/2017 |
| WO | WO-2017102446 A1 * | 6/2017 ............. A45D 34/04 |

OTHER PUBLICATIONS

English Specification of 10-2017-0043080.
English Specification of 10-1695411.
English Specification of 10-1706014.
English Specification of 10-1713583.
English Specification of 10-0962973.

* cited by examiner

BEAUTY TREATMENT WATER GENERATOR AND BEAUTY TREATMENT DEVICE USING SAME

TECHNICAL FIELD

The present disclosure relates to a beauty treatment device which allows micro-currents to flow into a skin while massaging the skin by using the beauty treatment device through which the micro-currents flows.

BACKGROUND ART

As a background technology, as shown in FIG. 13 of Korean Patent No. 10-0962973, a far infrared irradiation window 21 is included to be able to irradiate the infrared rays generated from a high-brightness LED lamp 30 configured to emit light by electric energy of a battery mounted to a body 10.

An ion head 20 in which ions are generated by the flow of micro-currents between two electrodes of the battery is installed to the front of the body.

The body mounted with the ion head is installed with a control PCB board 40, and is installed with a push button 11 for selectively supplying the electric energy of the high-brightness LED lamp and the ion head.

By rubbing the skin with a massager installed with a power indicator lamp 12 at a point adjacent to the push button, the related art describes the uniform rubbing with a massage after applying the whitening composition to the skin.

However, this relates to a beauty treatment device which applies the composition to the skin and then emits light, ions, and sounds by using the massager, which makes a big difference in the hassle and the effect.

The micro-currents are current values at which the skin hardly feels. This is a method of using an ionizer, that is, an ion phenomenon rather than stimulating the skin.

The micro-currents are weak currents of less than 1000M (1 mA), and the weak bio-currents of about 40 μA to 60 μA in the human body flows as a signal transmission operation between each organ.

As various therapeutic effects of micro-currents on the human body have been proven, they have received attention from the medical community.

The micro-currents have been proven to be effective in increasing the production of adenosine triphosphate (ATP), promoting fracture healing, improving blood circulation, relieving pain, and the like, and thus have been mainly utilized as the medical use mainly related to the physical therapy.

In general, micro-current devices for skin care have an apparatus for allowing current to flow through the end portion where the skin contacts in the form of the conductor. The micro-currents prove the improvement effect of the skin by flowing currents of about 25 mA of 1.9V, and the product is generally produced and distributed.

In addition, by using the function of the micro-currents with cosmetics as described above, it is also possible to increase the function of cosmetics. Recently, various types of beauty treatment devices using micro-currents as described above have been developed and are forming a large market even in the beauty market.

In particular, since new components are developed day by day, the trend of using both cosmetics and micro-currents in the function of cosmetics is prominent.

In particular, in order to maximize the function of cosmetics, some hospitals also use so-called a Microneedle Therapy System (MTS) configured to wound the skin by using a microneedle, that is, a minute needle and then to absorb functional cosmetics there.

However, since all of these methods have a problem of not integrating the real functional cosmetics and the micro-current device (for example, galvanic), for example, having the functional function at the same time, there has been inconvenience in which the devices need to be used again after using two products, that is, cosmetics at all times.

In addition, when using the functional cosmetics at the same time, in terms of the absorption problem, the micro-currents do not flow immediately after the skin lotion contacts the skin but the micro-current device is used after doing makeup, such that it could not solve the problem.

DETAILED DESCRIPTION OF THE INVENTION

Technical Problems

The present disclosure allows micro-currents to flow while applying beauty treatment water to a skin.

The micro-currents are allowed to flow through the skin by a conductor structure in which there are a ball and an integrated container through which the micro-currents according to the disclosure flow and a current is allowed to flow to the ball side.

The ball is formed of a sphere and is formed of a convex lens on the light exiting surface and is configured so that the light rays in the wavelength band beneficial to the human body can focus.

Means to Solve the Problems

For achieving the objects, the present disclosure has the following configurations.

a beauty treatment device, the beauty treatment device being composed of the upper portion and the lower portion, and the lower portion of the beauty treatment device is composed of a handle;

a hollow hole configured inside the upper portion of the beauty treatment device;

a conductive holder configured in the hollow hole; and a beauty treatment water generator detachably attachable to the conductive holder, when the beauty treatment water generator is inserted into the conductive holder and beauty treatment water flowing out of the beauty treatment water generator contacts a skin, at least a part of the beauty treatment water generator is formed of a conductor and is configured so that the micro-currents generated by the beauty treatment device and flowing through the beauty treatment water flow through the human skin through the conductive holder and the conductor.

Here, the conductive holder has a cylindrical shape.

Here, it is preferable that a handle conductor is configured on a part of the handle and micro-currents are configured to flow when the beauty treatment water flowing out of the beauty treatment water generator contacts the skin with grapping the handle conductor.

Here, it is preferable that the handle conductor flows positive currents and the conductor in a part of the beauty treatment water generator flows negative currents.

Here, the beauty treatment water generator is configured so that the beauty treatment water flows through a beauty ball.

Here, it is preferable that the beauty ball is formed of a sphere and is formed of a convex lens on a light exiting portion so that LED lights emitted from the beauty treatment device focus on one and light of the wavelength band beneficial to the human body penetrates the skin.

Here, a beauty treatment device, the beauty treatment device being composed of the upper portion and the lower portion, and the lower portion of the beauty treatment device is composed of a handle;

a hollow hole configured inside the upper portion of the beauty treatment device;

a conductive holder configured in the hollow hole; and a massage cap detachably attachable to the conductive holder, the massage cap being composed of a second conductor and an inserting part, when the massage cap is inserted into the conductive holder and the second conductor of the massage cap contacts a skin at least, the micro-currents generated by the beauty treatment device flow through the human skin through the conductive holder and the second conductor.

Here, the beauty treatment device further includes a vibration element, and thus has a configuration capable of performing the skin massage more effectively.

Here, the beauty treatment device further includes an LED controller switch, a laser ultrasonic controller switch, and a power on/off switch on the handle of the beauty treatment device.

In addition, a beauty treatment water generator is configured by including a container; and a beauty ball holder coupled with the container, the beauty ball holder is composed of a beauty ball and a ball guide, and a conductor case is formed on the exterior of the beauty ball holder.

Here, it is preferable that the beauty treatment water generator configures a ball cover configured to protect the beauty ball.

Here, it is preferable that the upper portion of the beauty ball holder is formed with a configuration configured to be inserted into the container, and the lower portion of the beauty ball holder is formed with the ball guide configured to insert the beauty ball.

Here, it is preferable that the conductor case is configured to extend to contact the beauty ball and configured so that micro-currents flow through beauty treatment water flowing out through the beauty ball.

It is preferable that the beauty ball is formed of a sphere and is formed of a convex lens on the light exiting surface so that light rays focus when light enters through a glass.

Advantageous Effects

The present disclosure forms the conductive structure in the general beauty ball to allow micro-currents to flow the rotating ball, thereby maximizing the function of the beauty treatment water of the functional cosmetics.

It is possible to use the micro-current devices, the functional skin lotion, and the functional essence cosmetics at the same time as the beauty treatment device, thereby eliminating the inconvenience of using the existing micro-current device and cosmetics separately, and to use the device and cosmetics in an integrated form, thereby maximizing the function of cosmetics.

BEST MODE TO PRACTICE THE INVENTION

Figure 1:
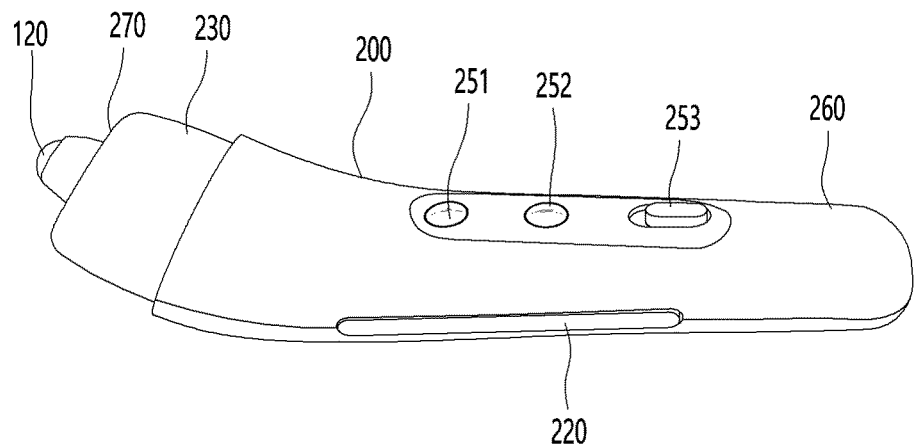
FIG. 1 is a configuration diagram showing the overall beauty treatment device.

Best Mode for carrying out the disclosure relates to a second embodiment of the present disclosure.

FIGS. 1 to 6 will be described.

a beauty treatment device 200, the beauty treatment device being composed of the upper portion and the lower portion, and the lower portion of the beauty treatment device being composed of a handle 260;

a hollow hole 270 configured inside the upper portion of the beauty treatment device;

a conductive holder 210 configured in the hollow hole; and a massage cap 300 detachably attachable to the conductive holder;

wherein the massage cap is composed of a second conductor 310 and an insertion part 320, when the massage cap 300 is inserted into the conductive holder 210 and the second conductor 310 of the massage cap contacts the skin at least, the micro-currents generated by the beauty treatment device are configured to flow the human skin through the conductive holder 210 and the second conductor 310.

A vibration element (not shown) is further configured. The vibration element is configured and the vibration is configured to be generated by the vibration element as soon as the power source is turned on (ON), thereby maximizing the massage effect.

As in a first embodiment, the second embodiment further configures an LED controller switch 252, a laser ultrasonic controller switch 251, and a power on/off switch 253 on the handle of the beauty treatment device to configure to perform the additional functions.

Next, the present disclosure relates to a beauty treatment water generator inserted into the hole 270 of the beauty treatment device, and is to invent that the micro-currents flow at the same time as soon as various beauty treatment water are added to contact the skin.

Mode for Carrying Out the Disclosure

The detailed description for carrying out the present disclosure will be explained with reference to the drawings as follows.

The following relates to a first embodiment.

Figure 2:
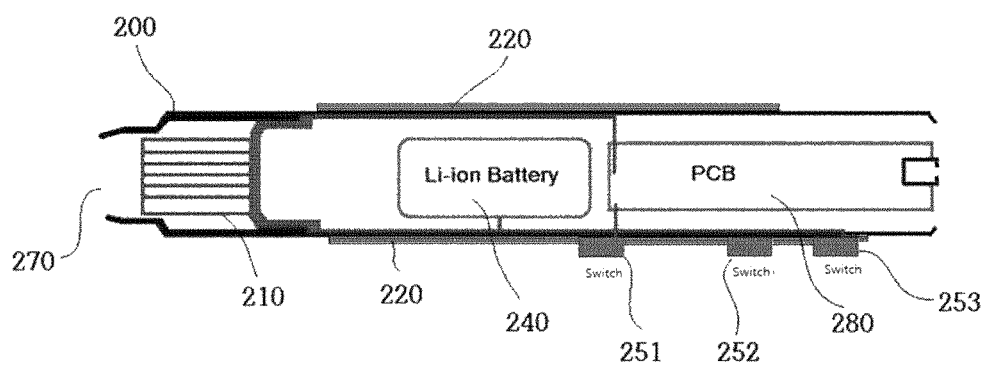
FIG. 2 is a diagram showing the interior of FIG. 1.

A description will be given with reference to FIGS. 1 to 3.

a beauty treatment device 200, the beauty treatment device being composed of the upper portion and the lower portion, and the lower portion of the beauty treatment device being composed of the handle 260;

the hollow hole 270 configured inside the upper portion of the beauty treatment device;

the conductive holder 210 configured to contact the hollow hole; and the beauty treatment water generator 100 detachably attachable to the conductive holder;

when the beauty treatment water generator is inserted into the conductive holder 210, at least a part of the beauty treatment water generator is composed of a conductor.

The present disclosure is composed of a conductor case 110 (FIG. 8) and configured so that the contact between the conductive holder 210 and the conductor case 110 occurs in any case.

Here, only the small conductor case 110 and the conductive holder 210 can also be configured as a contact point.

When the beauty treatment water flowing out of the beauty treatment water generator 100 contacts the skin, the micro-currents generated by the beauty treatment device and flowing through the beauty treatment water are configured to flow through the human skin through the conductive holder 210 and the conductor case 110.

Figure 3:
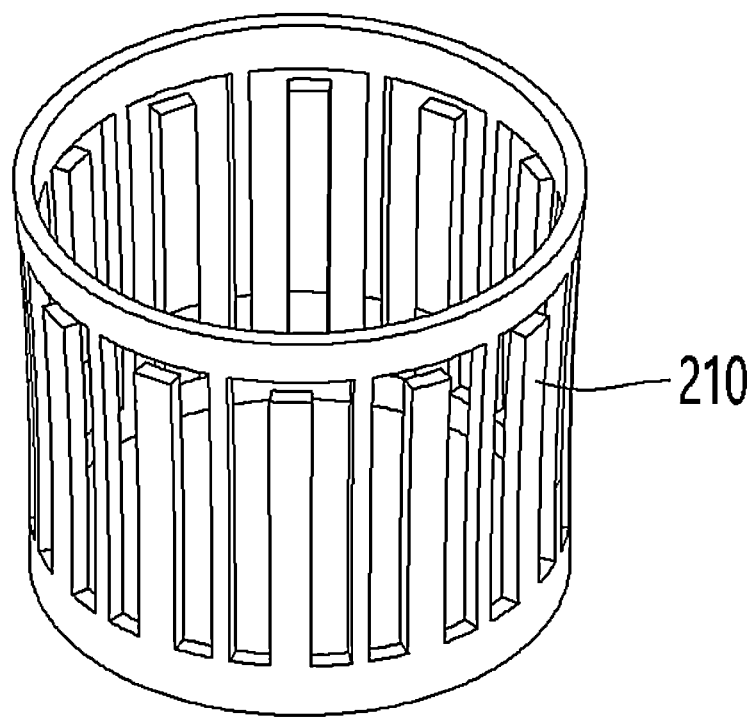
FIG. 3 is a diagram showing a conductive holder.
Figure 4:
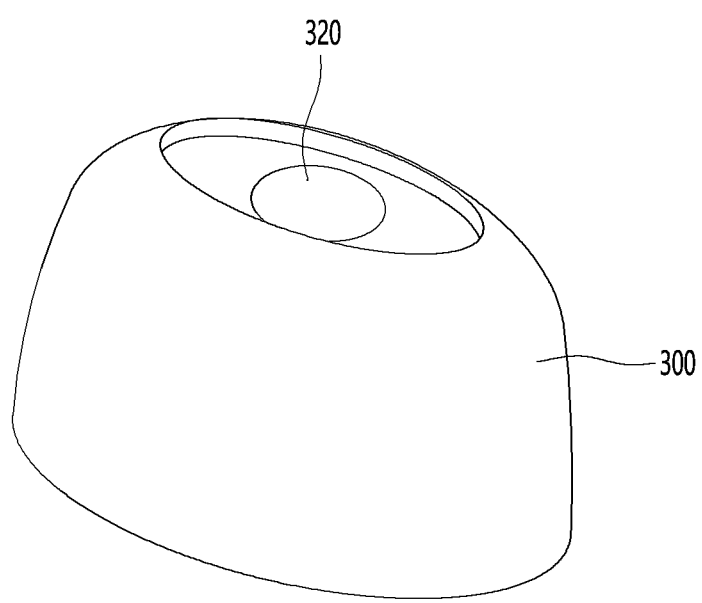
FIG. 4 is a diagram showing a massage cap.
Figure 5:
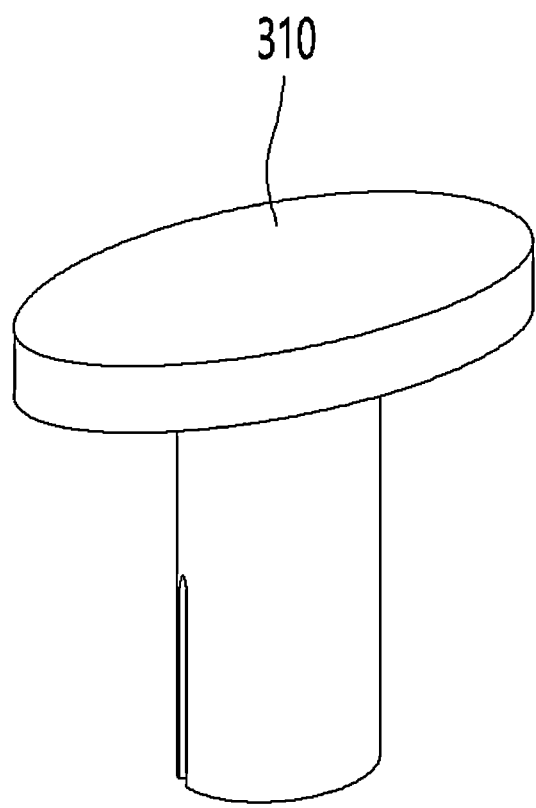
FIG. 5 is a diagram showing a second conductor coupled to a hole of a massage cap.
Figure 6:
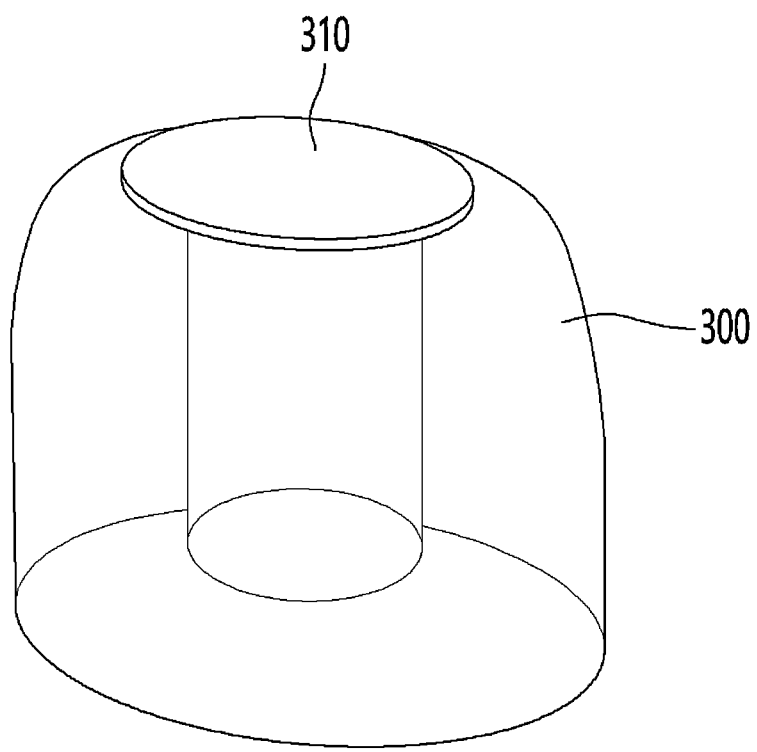
FIG. 6 is a diagram showing a configuration of coupling FIG. 4 with FIG. 5.

As shown in FIG. 3, the conductive holder 210 is configured to have a cylindrical shape to contact in any case.

Of course, the point contact which contacts by a point can be sufficient.

A handle conductor 220 is configured on a part of the handle and configured so that the micro-currents flow when the beauty treatment water flowing out of the beauty treatment water generator contacts the skin with grapping the handle conductor.

The beauty treatment water is configured to flow negative charges so that the beauty treatment water has an anion.

The present disclosure is configured to flow positive currents in the handle conductor 220 and to flow negative currents in the conductor case 110 of the beauty treatment water generator.

Of course, the effect also occurs even if the configuration is reversed.

The beauty treatment water generator 100 configures a beauty ball holder 140 so that the beauty treatment water flows through a beauty ball 120.

The beauty ball 120 is configured in a spherical shape to have a configuration of a convex lens on the light exiting surface and thus, is configured so that the light of the LED emitted from the beauty treatment device is concentrated into one and the light of the wavelength band beneficial to the human body penetrates the skin.

When the container 130 containing the beauty treatment water is made of glass or transparent plastic material, the LED light transmits the container containing the beauty treatment water to be incident to the beauty ball 120 and one light ray is configured to be converged on the skin so that the far infrared ray penetrates the skin well.

As a source of making the micro-currents, a battery has been composed of an ion battery 240 which is a secondary battery.

In addition, by configuring a PCB substrate 280, it is possible to exert the function of turning on/off micro-currents, the light ray, and the vibration element.

Three switches are configured and the number of switches can be increased or decreased in some cases.

The present disclosure is composed of the laser ultrasonic controller switch 251, the LED controller switch 252, the power on/off switch 253, and the like.

The following relates to the second embodiment.

FIGS. 1 to 6 will be described.

the beauty treatment device 200;

wherein the beauty treatment device is composed of the upper portion and the lower portion, and the lower portion of the beauty treatment device is composed of the handle 260, the hollow hole 270 configured inside the upper portion of the beauty treatment device;

the conductive holder 210 configured in the hollow hole; and the massage cap 300 detachably attachable to the conductive holder;

wherein the massage cap is composed of the second conductor 310 and the insertion part 320, when the massage cap 300 is inserted into the conductive holder 210 and the second conductor 310 of the massage cap contacts the skin at least, the micro-currents generated by the beauty treatment device are configured to flow through the human skin through the conductive holder 210 and the second conductor 310.

The vibration element (not shown) is further configured. The vibration element is configured and the vibration is configured to be generated by the vibration element as soon as the power source is turned on (ON), thereby maximizing the massage effect.

As in the first embodiment, the second embodiment further configures the LED controller switch 252, the laser ultrasonic controller switch 251, and the power on/off switch 253 on the handle of the beauty treatment device to configure to perform the addition functions.

Next, the present disclosure relates to the beauty treatment water generator inserted into the hole 270 of the beauty treatment device, and is to invent that the micro-currents flows at the same time as soon as various beauty treatment water are added to contact the skin.

The following corresponds to FIGS. 7 to 10 and will be described in detail with reference to the accompanying drawings.

the container 130;

the beauty ball holder 140 coupled to the container 130;

wherein the beauty ball holder 140 is composed of the beauty ball 120 and a ball guide 160, a beauty treatment water generator is manufactured by configuring the conductor case 110 to the exterior of the beauty ball holder 140 and the conductor case 110 is used for beauty by being inserted into a hole of any beauty treatment device.

Of course, when this beauty treatment water generator rubs the skin by opening the ball cover 150, the beauty treatment water is absorbed into the skin.

The ball cover 150 is configured to protect the beauty ball 120.

The conductor case 110 configures a screw 112 and the ball cover 150 also configures the corresponding screw 112 to configure to be screw-coupled to each other.

Of course, they can also be configured by forcibly fitting.

Even if the beauty treatment water is present in the container, it does not flow out through the beauty ball 120 due to the surface tension.

The central portion of the beauty ball holder 140 is formed of a step configuration for inserting the container 130, The upper portion of the beauty ball holder 140 is formed with the ball guide 160 for inserting the beauty ball 120.

The conductor case 110 is configured to extend to contact the beauty ball 120 and thus, is configured so that the micro-currents flow through the beauty treatment water flowing out through the beauty ball.

Accordingly, at the moment of applying the beauty treatment water to the skin, the micro-currents flowing through the beauty treatment water flow and are configured to show an excellent effect on beauty.

The beauty ball 120 of the beauty treatment water generator is formed in a spherical shape to serve as a convex lens on the light exiting surface.

Figure 7:
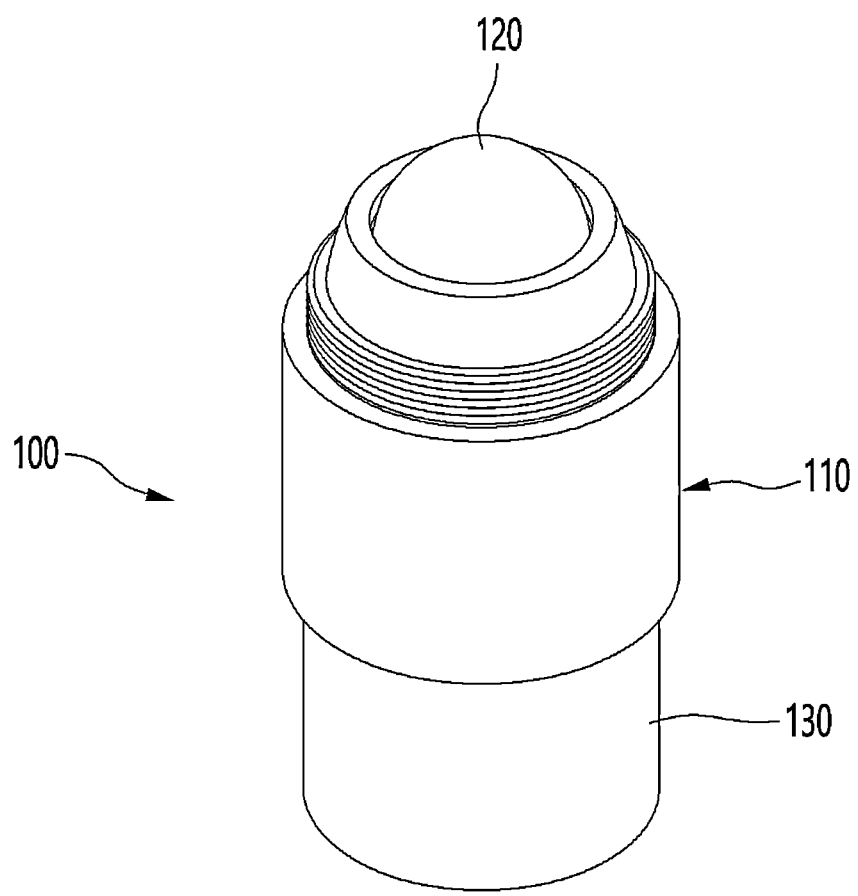
FIG. 7 is a diagram showing a beauty treatment water generator.

FIG. 7 is a configuration diagram showing the overall beauty treatment water generator 100.

Figure 8:
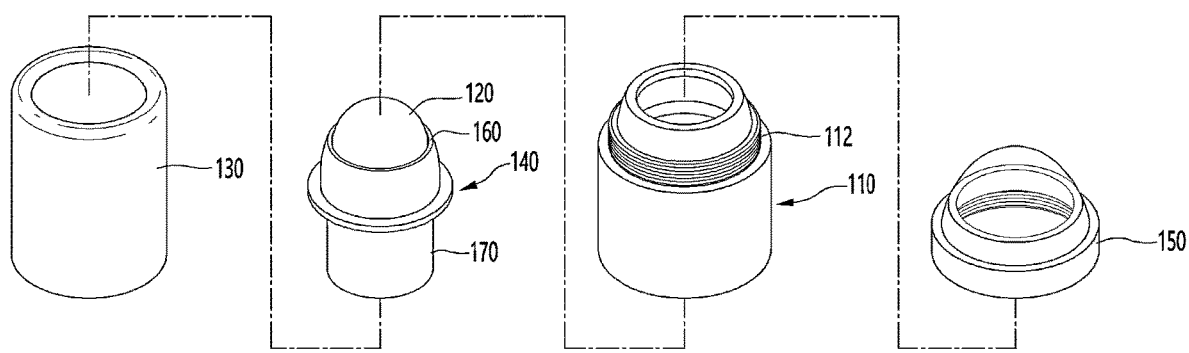
FIG. 8 is an exploded diagram of FIG. 7.

FIG. 8 is an exploded configuration diagram of the overall beauty treatment water generator of FIG. 7.

In the present disclosure, the beauty treatment water generator is composed of four components.

The beauty treatment water generator is composed of the container 130, the beauty ball holder 140 including the beauty ball 120, the conductor case 110, and the ball cover 150. An end 170 of the beauty ball holder 140 is configured to be inserted into a container 130.

In some cases, the number of components can be reduced.

Figure 9:
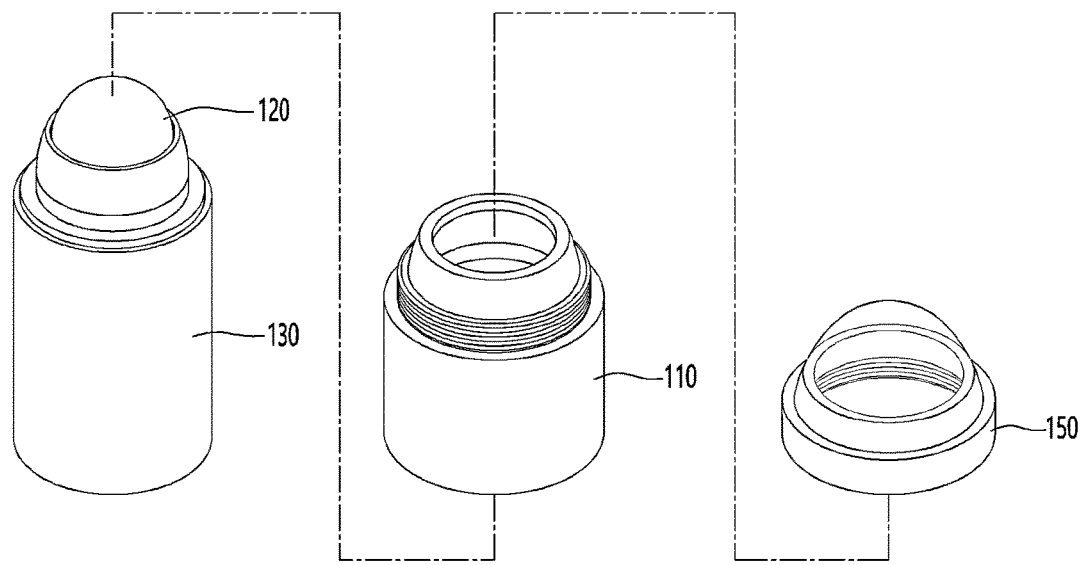
FIG. 9 is a diagram of coupling a beauty ball holder to a container.

FIG. 9 is a diagram showing that the beauty ball holder 140 including the beauty ball in the container 130 is inserted.

Figure 10:
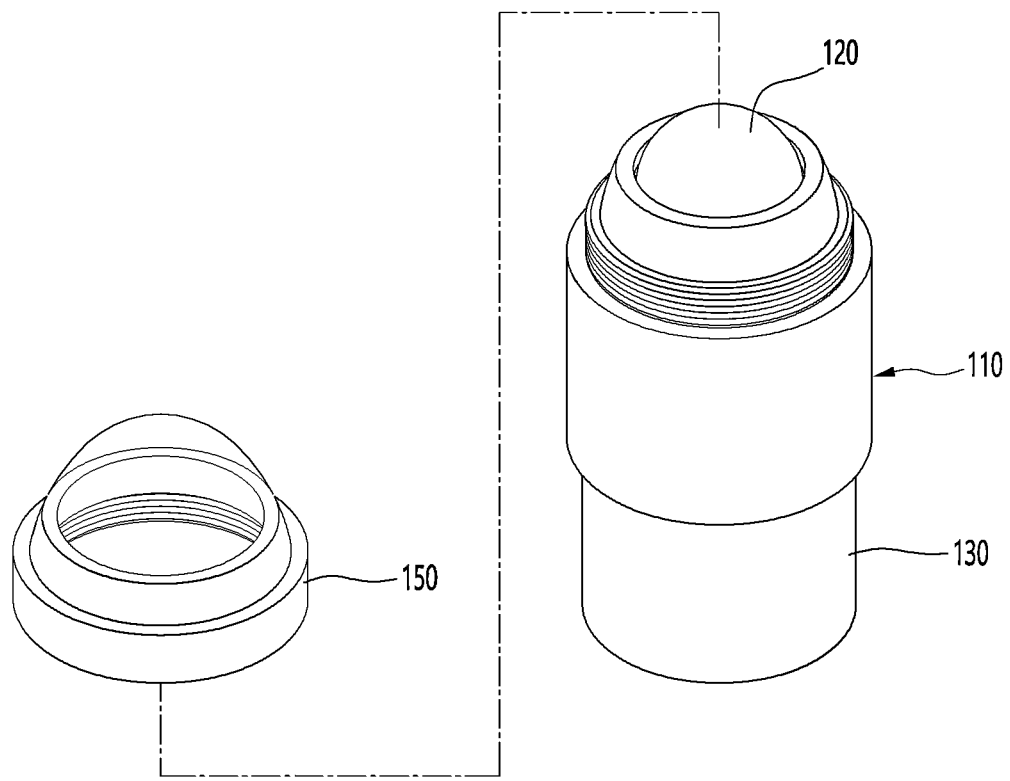
FIG. 10 is a diagram of coupling a conductor case to FIG. 9.

FIG. 10 is a diagram showing that the conductor case 110 is inserted into FIG. 9.

The ball cover is used when not using or storing the beauty treatment water generator and when using the beauty treatment water generator, the ball cover is released and the beauty treatment water generator is used by being inserted into the hole of the beauty treatment device.

The beauty treatment water generator is used for one time use and can be manufactured by using an ampoule.

And then, when rubbing the beauty ball on the skin, the beauty treatment water contacts the skin while the beauty ball rotates, and the micro-currents flow together with the beauty treatment water flowing out of the beauty treatment device and the beauty effect is appeared as soon as the beauty treatment water is well absorbed into the skin by irradiating the skin with the light rays, thereby eliminating wrinkles on the wrinkled skin.

Figure 11:
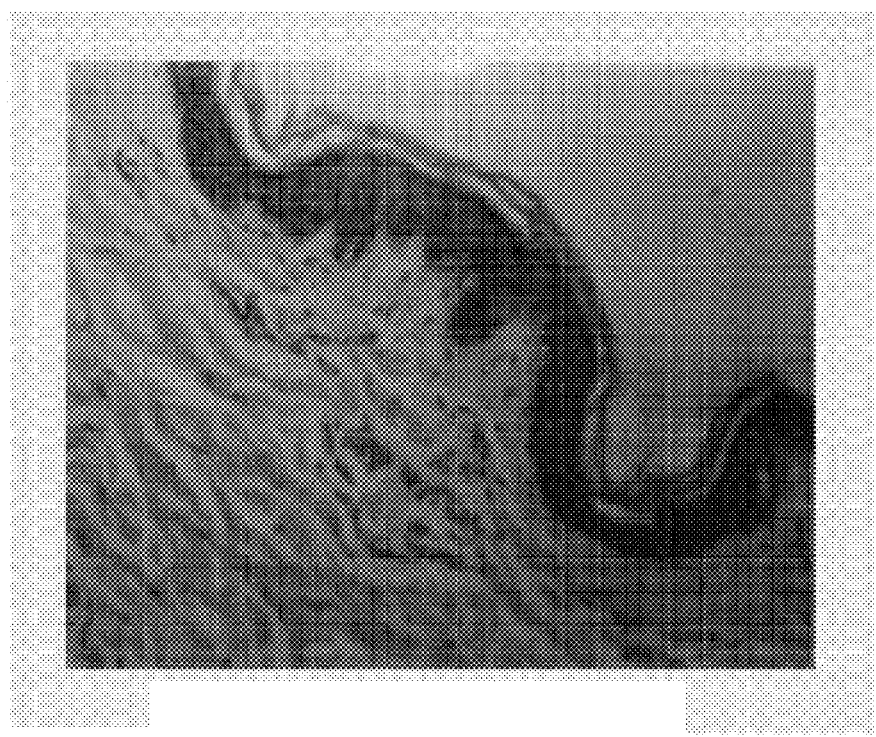
FIG. 11 is a diagram showing before using the beauty treatment water generator.
Figure 12:
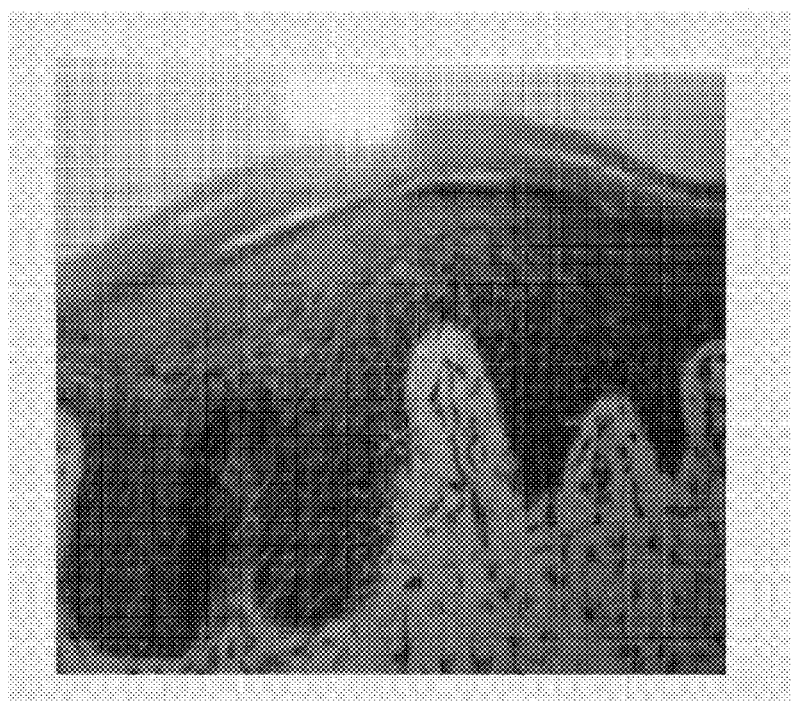
FIG. 12 is a diagram showing improving wrinkles after using the beauty treatment water generator.
Figure 13:
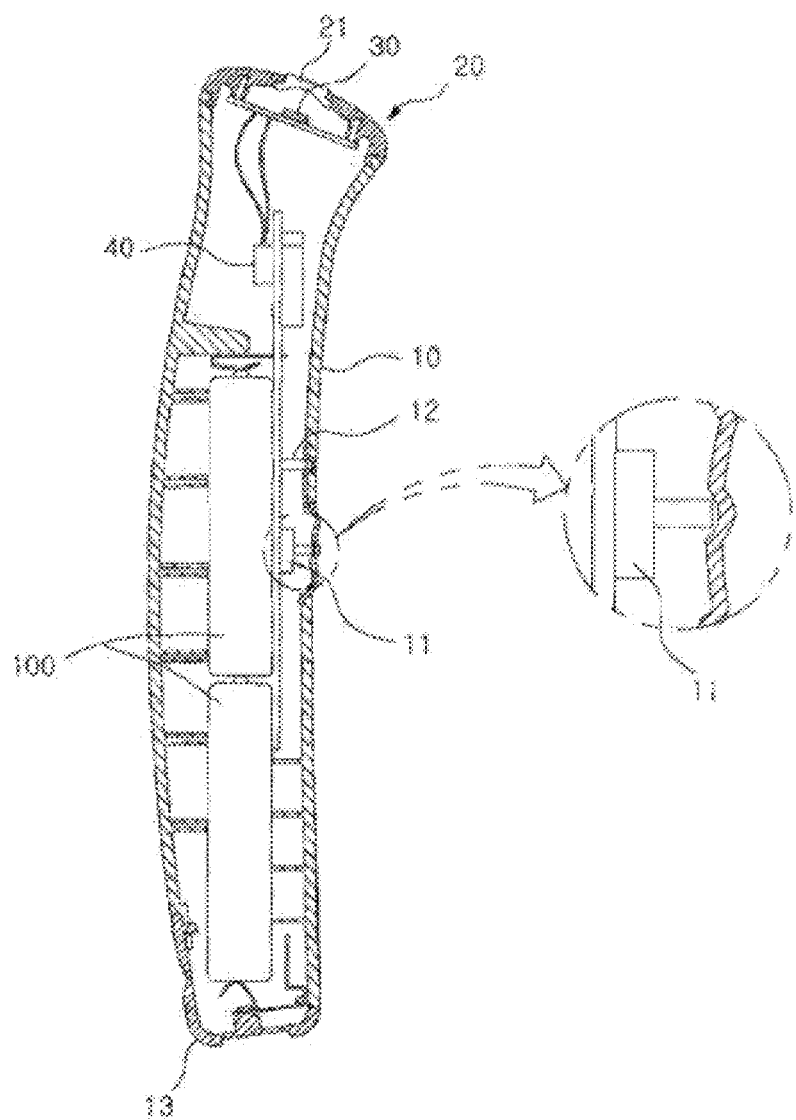
FIG. 13 is a diagram of the related art.

FIGS. 11 and 12 are diagrams showing before and after using the beauty treatment device and diagrams showing that wrinkles are improved.

The vibration element can be configured to be able to vibrate as soon as the switch is turned on (ON), thereby allowing the beauty treatment water of the liquid contained in the container to flow out of the beauty ball well.

In addition, since the beauty ball rotates while contacting the skin, the beauty treatment water flows through the surface of the beauty ball to contact the skin.

Of course, the effect of the vibration element also appears to shock the skin.

The vibration element uses a typical element.

LED light rays are mainly composed of far infrared rays, and the beauty ball is formed in a spherical shape so that the far infrared rays focus on the skin.

In addition, the mold is configured so that the spherical-shaped beauty ball 120 is not separated from the beauty ball holder 140 and the transparent beauty ball is exposed to the ball guide 160 by about 40%.

The terms or words used in the present specification and the claims should not be construed as limiting in their usual or dictionary meanings, and should be construed as meanings and concepts corresponding to the technical spirit of the present disclosure based on the principle that the inventor can appropriately define the concept of terms in order to describe his/her disclosure in the best method.

Accordingly, since the configuration shown in the embodiments and the drawings described in the present specification are only the most preferred embodiment of the present disclosure, and do not represent all of the technical spirit of the present disclosure, it should be understood that these can be replaced with various equivalents and variations.

INDUSTRIAL APPLICABILITY

The present disclosure relates to the beauty treatment device which allows the micro-currents to flow to the skin while massaging the skin by using the beauty treatment device through which the micro-currents flow, and relates to a technology which can be industrially used to maximize the beauty treatment water function of the functional cosmetic.

The invention claimed is:

1. A beauty treatment device having an upper portion and a lower portion comprising:
a handle configured on the lower portion;
a hollow hole configured inside the upper portion;
a conductive holder configured in the hollow hole; and
a beauty treatment water generator detachably attachable to the conductive holder which is cylindrical;
wherein the beauty treatment water generator comprises a container, a beauty ball holder and a conductor case,
wherein the beauty ball holder connected to the container comprises a beauty ball which is spherical and a ball guide,
wherein a lower portion of the beauty ball holder is configured to be inserted into the container
wherein an upper portion of the beauty ball holder is formed with the ball guide to insert the beauty ball,
wherein the conductor case is inserted into the exterior of the beauty ball holder connected to the container,
wherein the conductor case is configured to extend to contact the beauty ball and thus, is configured so that micro-currents flow through the beauty treatment water flowing out through the beauty ball,
wherein the beauty treatment water generator is configured so that the beauty treatment water flows through the beauty ball,
wherein the micro-currents generated by the beauty treatment device and flowing through the beauty treatment water are adapted to flow through a human skin through the conductive holder and the conductor case, when the beauty treatment water flowing out of the beauty treatment water generator is adapted to contact the human skin, and
wherein a handle conductor is configured on a part of the handle and the micro-currents are configured to flow when the beauty treatment water flowing out of the beauty treatment water generator is adapted to contact the human skin with grasping the handle conductor.

2. The beauty treatment device of claim 1,
wherein the handle conductor flows positive currents and the conductive holder flows negative currents.

3. A beauty treatment device having an upper portion and a lower portion comprising:
- a handle formed on the lower portion;
- a switch formed on the handle;
- a hollow hole configured inside the upper portion;
- a conductive holder configured in the hollow hole; and
- a massage cap detachably attachable to the conductive holder which is cylindrical, the massage cap being composed of an inserting part and a second conductor inserted into the inserting part;
- wherein a part of the second conductor is a convex cap adapted to contact a human skin, and an other part of the second conductor is in form of a cylinder that is inserted into and in close contact with an inner side of the conductive holder,
- wherein, when the convex cap of the second conductor is adapted to contact the human skin, micro-currents are adapted to flow through the human skin through the conductive holder and the second conductor,
- wherein a handle conductor is configured on a part of the handle and the micro-currents are configured to flow when the convex cap of the second conductor is adapted to contact the human skin with grasping the handle conductor.

4. The beauty treatment device of claim 3, further comprising a vibration element.

5. The beauty treatment device of claim 3,
wherein the handle conductor flows positive currents and the conductive holder flows negative currents.

* * * * *